United States Patent [19]

Spinelli et al.

[11] Patent Number: 5,413,593
[45] Date of Patent: May 9, 1995

[54] USING SUB-THRESHOLD UNIPOLAR PACING MARKERS TO IMPROVE THE INTERPRETATION OF SURFACE EKG IN PACEMAKER PATIENTS

[75] Inventors: Julio C. Spinelli; Jesse Hartley, both of Shoreview; Jan P. Heemels, Minneapolis, all of Minn.

[73] Assignee: Cardiac Pacemakers, Inc., St. Paul, Minn.

[21] Appl. No.: 188,821

[22] Filed: Jan. 31, 1994

[51] Int. Cl.$^6$ .............................................. A61N 1/37
[52] U.S. Cl. .......................................... 607/27; 607/36
[58] Field of Search ...................... 607/27, 28, 36, 37; 128/696

[56] References Cited

U.S. PATENT DOCUMENTS

| | | | |
|---|---|---|---|
| 4,164,227 | 8/1979 | Auerbach | 607/27 |
| 4,374,382 | 2/1983 | Markowitz . | |
| 4,388,927 | 6/1983 | Schober . | |
| 4,548,209 | 10/1985 | Wielders et al. . | |
| 4,550,370 | 10/1985 | Baker . | |
| 4,559,947 | 12/1985 | Renger et al. . | |
| 4,595,009 | 6/1986 | Leinders . | |
| 4,601,291 | 7/1986 | Boute et al. . | |
| 4,969,467 | 11/1990 | Callaghan et al. | 607/28 |
| 5,127,401 | 7/1992 | Grevious et al. . | |

OTHER PUBLICATIONS

Biotronik Ergos 03—"Rate Adaptive Dual Chamber Pacemaker Controlled by Motion Energy"—Preliminary Technical Manual, p. 15.

*Primary Examiner*—William E. Kamm
*Assistant Examiner*—Kennedy J. Schaetzle
*Attorney, Agent, or Firm*—Haugen and Nikolai

[57] ABSTRACT

A pacemaker including a marker code generator generating marker codes between an indifferent electrode disposed on the pacemaker housing and the pacemaker can serving as a reference electrode. Marker code signals are generated proximate the pacemaker rather than proximate cardiac tissue, and thus can be generated at a large potential for sensing by surface EKG, and can also be generated simultaneously while pacing the heart and not necessarily in the refractory period. The pacemaker facilitates the interpretation of surface EKG, and can be sensed and recorded by commercially available two-channel holter monitors which can be taken home with the patient. Thus, marker code signals can be sensed and recorded while at home and played back for the physician at a later time for analysis. The marker code generator can be selectively turned on by the external programmer such that battery life depreciation is not appreciable. The pacemaker can be adapted with either a unipolar or bipolar endocardial lead.

8 Claims, 1 Drawing Sheet

USING SUB-THRESHOLD UNIPOLAR PACING MARKERS TO IMPROVE THE INTERPRETATION OF SURFACE EKG IN PACEMAKER PATIENTS

BACKGROUND OF THE INVENTION

1. Field of the Invention

The present invention relates generally to cardiac pacemakers, and more particularly to cardiac pacemakers having a markers channel corresponding to and indicative of pacing events of the pacemaker.

2. Background of the Prior Art

During unipolar and bipolar pacing, the pacing spike may be hard to ascertain in the surface EKG. Thus, the resulting electrocardiogram many times does not permit a physician the ability to interpret the behavior of the implanted pacemaker to evaluate the adequacy of the therapy that is being delivered to the patient. At high pacing rates the analysis is even more difficult, and the task of distinguishing between atrial paced or sensed beats becomes sometimes formidable. Another problem is to know why the pacemaker is delivering a given therapy. Situations like "fall-back", "rate smoothing", "sensor rate", "sensing during refractory", "upper rate limit behavior", etc. are also very difficult to interpret from surface EKG.

Prior art pacemakers typically incorporate telemetered marker channels to help interpret pacemaker behavior, which marker channels include coding generated concurrently by the pacemaker during pacing. Presently, the marker channel is sensed using well-defined external devices in combination with telemetry functions built into the pacemaker. The marker channel provides coded information indicative of the pacemaker therapy currently being applied to the heart such that the attending physician can intelligently compare the ascertained EKG to the pacing therapy being applied by the pacemaker.

The ERGOS 03 pacemaker offered by Biotronik provides the ability to use a marker channel by sending below-stimulation threshold pulses to the endocardial electrodes immediately after pacing, which pulses can be recognized on a surface EKG. Atrial sensed events are marked by a 30 $\mu S$ pulse that is emitted by the atrial lead. Ventricular sensed events are marked by two sequential marker signals emitted by the ventricular lead. The two ventricular pulses have a spacing of 60 milliseconds, the first denoting the moment of the sensed event. This particular system has two main disadvantages. First, during committed pacing situations issuing a sub-threshold pacing pulse to the ventricular or atrial leads, a transitory conduction block can occur. Issuing a supra-threshold pacing pulse immediately thereafter could cause arrhythmias. Secondly, this scheme only allows the pacemaker to send markers to the surface EKG during sensing, and does not provide enough resolution or time to code in several markers to indicate situations like atrial sensed during PVARP, pacing due to rate smoothing, ventricular ectopic sensing, etc. Moreover, this scheme does not allow the pacemaker to send markers simultaneously while pacing the heart. Finally, this scheme does not allow generating supra-threshold markers.

Several patents issued to Medtronic teach pacemakers incorporating marker channels using well-known telemetry functions. However, these devices require telemetry equipment and receivers, and diagnosis needs to be performed in the presence of an attending physician with the appropriate equipment and telemetry receivers. Thus, patients who feel irregularities in their pacemaker operation only occasionally and intermittently at home cannot be properly diagnosed by a physician for adjustments to their pacemakers. Prior art pacemakers having marker functions are taught in U.S. Pat. No. 4,550,370 and U.S. Pat. No. 4,548,209 to Medtronic. Each of the devices taught implements telemetry for transmission of programming codes and to receive marker information from the pacemaker for remote display and utilization. Similarly, U.S. Pat. No. 4,595,009 and U.S. Pat. No. 4,374,382 also to Medtronic teach marker channel telemetry systems for medical devices, as do U.S. Pat. Nos. 4,601,291 and 4,559,947.

To help understand the behavior of a pacemaker which may be operating in an unknown manner, the physician will provide the patient with a multi-channel holter monitor to sense and store EKG signals over an extended time period, such as 24 hours, while the patient is at home and away from the physician's office. Unfortunately, prior art diagnostic methods using holter monitors only sense and store EKG signals from one or more locations of a patient's body, which EKG signals are subsequently studied by the physician. Consequently, the physician's ability to diagnose the pacemaker behavior is limited to study of the recorded EKG signals since telemetry of the marker channels cannot be ascertained to help a physician understand the pacemakers behavior.

OBJECTS

It is accordingly a principle object of the present invention to provide a pacemaker capable of generating marker channels without using telemetry, which markers can be recorded by the patient at home.

It is a further object of the present invention to provide a pacemaker having marker channels which can be easily sensed in the surface EKG of the patient.

Still yet a further object of the present invention is to provide a pacemaker having marker channels which does not create the possibility of producing a transient conduction block that could lead to ventricular arrhythmias.

Still yet another object of the present invention is to provide a pacemaker having marker channels which can be tuned to the bandwidth of the receiver such as an EKG device, thus providing the possibility of encoding most of the available markers to the surface EKG.

It is another object of the present invention to provide a pacemaker having marker current/voltages generated remote from the cardiac tissue and thus can have an increased signal strength without risk of producing a heart contraction.

Still yet a further object of the present invention is to provide a pacemaker having a marker channel which can be generated at any time including simultaneously during the generation of pacing pulses.

SUMMARY OF THE INVENTION

The foregoing objects and advantages are achieved by providing a cardiac pacemaker having an electrode disposed proximate but isolated from the pacer can, wherein the pacemaker has a marker code generator coupled to both the pacer can and the electrode for generating marker codes therebetween indicative of the pacemaker pulse generator activity. Thus, the marker generator generates electrical signals proximate the pacemaker can itself rather than proximate cardiac tissue. The marker codes are generated at a sufficient strength such that they can be detected by surface EKG. Accordingly, a standard two-channel holter monitor can be utilized by a patient at home to sense and store EKG on one channel, and sense and store a marker channel on the second channel simultaneously. These signals can be recorded over an extended period of time such as 24 hours and then played back for the attending physician at a later time for analysis. The marker channels which are recorded simultaneously with the EKG signal provide the physician valuable information on the pacemaker therapy which was applied when the signals were sensed. This marker channel information helps the physician understand what therapy was being applied, and why the pacemaker was providing a particular therapy.

More specifically, the cardiac pacemaker comprises a pacer housing including a conductive pacing can. A first endocardial lead having a first electrode is disposed thereon. A second electrode is disposed proximate the housing and is insulated from the pacer can. A pulse generator is coupled to the endocardial lead for generating pacing pulses. A marker generator is coupled to both the pacer can and the second electrode for generating marker codes therebetween. The marker codes are indicative of the pace generator activity, wherein the marker codes are generated at a sufficient signal strength such that they can be detected by surface EKG. Since the marker codes are generated proximate the pacer can itself, the marker codes do not affect cardiac tissue and thus can be generated at a sufficiently large signal and at any time, even during pacing of the heart.

Ideally, the second electrode is disposed on the pacer housing and is insulated from the pacer can, and may comprise of a button electrode. The marker codes are preferably generated at an electrical potential of between 5 millivolts and 5 volts. The first endocardial lead can have a single tip electrode disposed in the heart ventricle wherein the pacer can serves as a reference electrode. Alternatively, the endocardial lead can be provided with a ring electrode as well which is disposed in the heart ventricle. Thus, unipolar or bipolar pacing can be provided while generating a marker channel proximate to the pacemaker can. The patient's body serves as the transmitting medium conducting the marker codes between the pacemaker and the patient's skin. Thus, conventional EKG devices including portable two-channel holter monitors can be implemented to sense and store the marker codes along with the surface EKG.

DESCRIPTION OF THE PREFERRED EMBODIMENT

Cross-reference is made to the pending application assigned to the assignee of this application having U.S. patent application Ser. No. 07/698,789, filed May 13, 1991, and entitled "Dual Indifferent Electrode", which is incorporated herein by reference.

Figure 1:
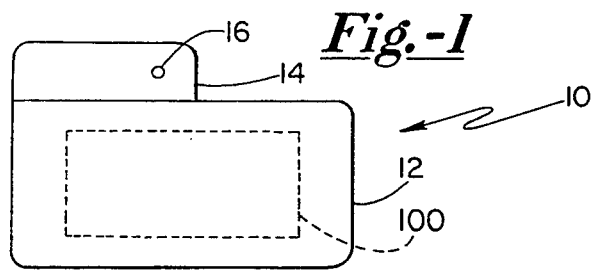
FIG. 1 schematically shows a pacer apparatus having a dual indifferent electrode apparatus.

Referring to FIG. 1 there is diagrammatically shown a side view of a pacemaker apparatus 10 comprised of a conductive metal can 12 and an insulating plastic top or header 14. Mounted in the top 14 and isolated from the metal can 12 is a button electrode 16. Contained within the can 12 is an electronic circuit 100 which is explained in more detail below and which comprises pacemaker circuitry including a marker code generator.

Figure 2:
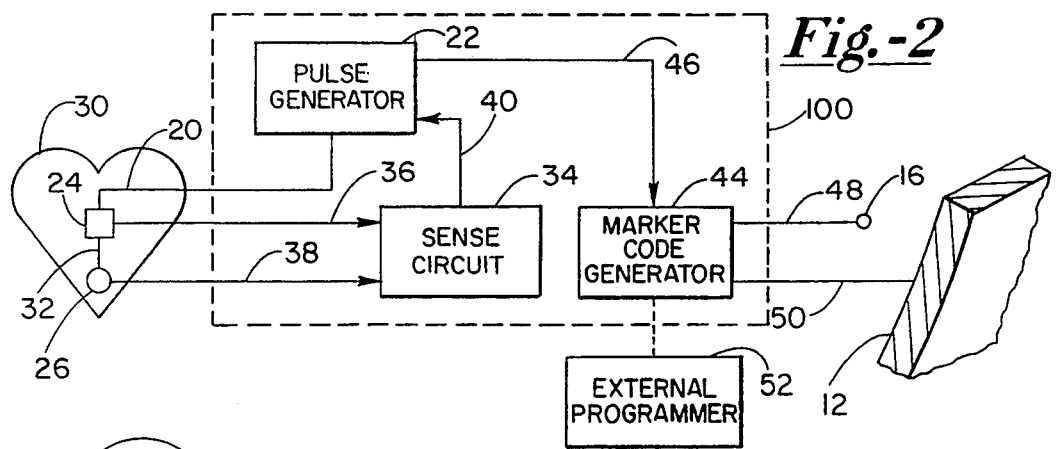
FIG. 2 schematically shows one embodiment of a dual indifferent electrical apparatus for use in an implantable heart pacemaker with a marker code generator disposed between a neutral button electrode and the pacemaker can.

Now referring to FIG. 2, the circuit 100 is shown in more detail. An endocardial lead 20 is connected to a pulse generator 22 which is contained within the pacemaker 10. The lead 20 includes electrodes 24 and 26 located within one of the chambers of the heart 30. Electrode 26 may be, for example, a stimulating tip electrode on a catheter-type lead disposed in a ventricle while electrode 24 may be, for example, a ring electrode disposed also in the ventricle. Insulator lead body 32 mechanically supports electrodes 24 and 26. A sensing circuit 34 is electrically coupled to both electrodes 24 and 26 via sensing lines 36 and 38, respectively, and comprises of any well-known sensing circuits for sensing and processing electrical signals from the electrodes disposed within the heart. Sensing circuit 34 is electrically coupled to pulse generator 22 via line 40, wherein microprocessor based pulse generator 22 generates pacing pulses to electrodes 24 and 26 in response to sensing circuit 34 based on an algorithm programmed therein. The pacing circuitry discussed so far is well-known in the art.

Also comprising a portion of circuit 100 is a marker code generator 44 which generates marker codes indicative of the pacemaker state in response to pulse generator 22, which pulse generator 22 is monitored via line 46. Marker code generator 44 can comprise of any well-known marker code generators, including amplitude or pulse-width modulated devices, such as those disclosed and discussed in the cited prior art, which prior art references are incorporated herein by reference. For instance, one pulse can be generated to indicate an atrial event, and two pulses to indicate a ventricular event. Many algorithms are possible and suitable with the present invention.

Button electrode 16 has a surface area typically on the same order of magnitude as the surface area of ring electrode 24 and is advantageously disposed on the plastic top 14 of the implantable pacemaker 10. In the embodiment of FIG. 2, the button electrode 16 is connected via lead 48 to marker code generator 44. The conductive metal pacemaker can 12 also serving as an electrode is electrically connected to marker code generator 44 via lead 50.

In contrast to prior art pacemakers which generate marker codes transmitted via telemetry, the present invention is comprised of a pacemaker generating unipolar marker codes between an indifferent electrode 16 and the pacemaker can 12. Thus, the marker codes are generated proximate the pacemaker itself and remote from cardiac tissue. These unipolar pulses are generated between the can of the pacemaker 12 and the indifferent electrode 16 at a potential exceeding the potential which could cause a heart contraction. Further, the marker codes can be and preferably are generated simultaneously as pacing pulses are being applied by pulse generator 22 to electrodes 24 and 26 within heart 30. This provides the possibility of encoding more markers due to the expanded time frame available for sending markers. Further yet, this invention provides the possibility of sending the markers to the surface EKG wherein the pulses have a high energy, preferably in the range of 500 millivolts to 1 millivolt. Moreover, the generation of the pulses can be tuned to the bandwidth of the receiver, and in the case of the surface EKG, 0.1 to 100 Hz. These marker pulses can have different shapes, amplitudes, durations and/or polarities to produce different types of marks in the surface EKG recorder, which marker codes are generated in such a way as to characterize the behavior of the pacemaker therapy being applied to electrodes 24 and 26.

A further feature of the present invention is that the marker code generator 44 can only be activated when turned on by the external programmer 52 operated by the physician, such as using magnetic switches. Thus, the physician can selectively enable the marker code generator 44 for diagnostic purposes such as when a standard two-channel or multi-channel holter monitor is adapted to the patient and taken home by the patient for monitoring over an extended time period of say 24 to 48 hours. Thus, the pacemaker battery life will not be appreciable reduced as the marker code generator 44 is only selectively implemented by the physician using external programmer 52.

Using the metal can of the pacemaker 10 along with an indifferent electrode 16 to encode information in the form of marker spikes in the surface EKG provides the feature of sending information about the state of the pacemaker to the physician while using the body as the link and the surface EKG as the receiver. This approach has the advantage over the prior art sub-threshold pacing spikes since it does not risk the possibility of producing a transient conduction block that could lead to ventricular arrhythmias, as discussed by KATZ (Physiology of the Heart, Raven Press, New York, N.Y., 1992, pgs. 446–447). As discussed by KATZ, transient conduction blocks could otherwise occur if marker codes are generated proximate cardiac tissue because the voltage-dependence of the heart's cells sodium inactivation gates, a sub-threshold depolarization (like a sub-threshold pacing spike "marker", being sent using the unipolar configuration) followed by a supra-threshold stimulus "normal pacing spike" will yield in an action potential which rises more slowly than the normal action potential and is of smaller amplitude. KATZ claims that this voltage-dependence behavior will give rise to conduction blocks that could produce ventricular arrhythmias.

Another advantage of the present invention is the ability to tune bandwidth of the pacing spikes to the bandwidth of the receiver i.e. EKG device, thus providing the possibility of encoding most of the available markers to the surface EKG.

By generating marker codes between the pacer can 12 and the indifferent button electrode 16 adjacent the pacemaker 10, the physician is better able to interpret the behavior of the pacemaker and thus evaluate the adequacy of the therapy that is being delivered to the patient in view of the marker codes generated simultaneously while pacing the heart, which codes can be sensed in the surface EKG. Even at higher pacing rates the analysis can be conducted, and even the formidable task of distinguishing between atrial paced or sensed beats becomes easy. Further, the physician is able to ascertain why the pacemaker is delivering a given therapy, including situations like "fall-back", "rate smoothing", "sensor rate", "sensing during refractory", "upper rate limit behavior", "mode switching", etc. Thus, this invention is directed towards providing a tool that will let the physician simplify the interpretation of pacemaker behavior by the surface EKG.

Figure 3:
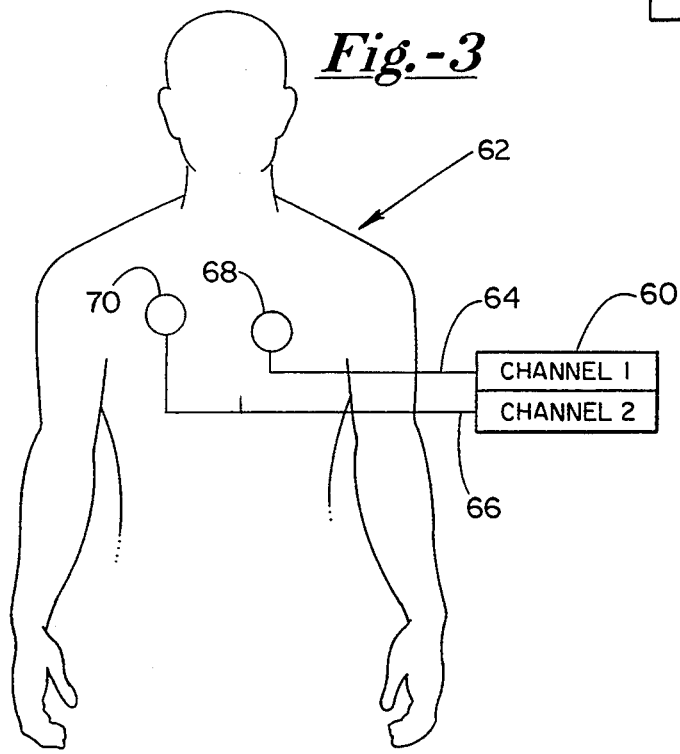
FIG. 3 is a pictorial representation of a standard two-channel holter monitor with two EKG leads adapted to a patient's chest proximate the heart and pacemaker for recording surface EKG signals and marker codes.

Referring now to FIG. 3, a commercially available holter monitor 60 is shown connected to a patient 62 via a pair of commercially available EKG leads 64 and 66. Each lead 64 and 66 is electrically coupled to an EKG sensing pad 68 and 70, respectively. EKG electrode 68 is coupled to channel 1 of holter monitor 60, and EKG electrode 70 is connected to channel 2. Electrode 68 is disposed proximate the heart for sensing surface EKG, and second electrode 70 is disposed proximate pacemaker 10 surgically implanted within patient 62 for sensing marker codes.

Figure 4:
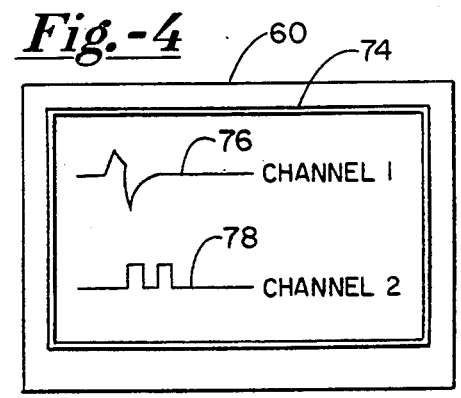
FIG. 4 is a pictorial representation of a standard two-channel holter monitor displaying two channels of information, first, an EKG signal, and secondly, marker codes which are simultaneously generated with the sensed surface EKG.

Referring now to FIG. 4, holter monitor 60 is shown having a two-channel display 74 visually displaying the first channel 76 displaying the EKG sensed proximate the patient's heart, and the second channel 78 displaying the marker code spikes sensed proximate pacemaker 10. Each of the channels is displayed in real time, simultaneously, such that the attending physician can play back the recorded sensed EKG signals of the patient while analyzing the marker codes, simultaneously, so that the physician can understand what therapy was being applied by the pacemaker when the particular EKG signal was sensed.

Since commercially available two-channel or multi-channel holter monitors 60 are commercially available, no further external equipment needs to be designed for application with the present invention. Rather, monitoring equipment is already available off-the-shelf and is ideally adapted to be used with the present invention. Most pacemakers, including demand-type pacemakers are ideally suited to implemented the present invention of an additional indifferent electrode, such as button electrode 16, along with the disclosed marker code generator 44 electrically coupled to button electrode 16 and pacemaker can 12. Again, any well-known marker algorithm or coding scheme, such as that disclosed by the prior art references which are incorporated herein by reference, can be implemented in pacemaker marker code generator 44.

While the present invention is shown implemented with a bipolar lead, it is also to be recognized by one of ordinary skill in the art that unipolar pacing could be provided as well with a single tip electrode 26 and the pacemaker can 12 serving as a second reference electrode. The invention can also be implanted in a dual chamber pacemaker. Thus, the present invention is ideally suited for unipolar or bipolar pacing therapy.

Further, while an integral indifferent button electrode 16 is shown disposed on pacemaker housing 10, it is also to be recognized a separate lead could be used as well extending to an indifferent electrode which is disposed proximate pacemaker can 12, and thus limitation to an indifferent electrode defined on the pacemaker can housing is not to be inferred. Moreover, a second lead extending to a second indifferent electrode could be provided in place of pacemaker can 12 such that marker signals could be generated therebetween proximate the pacemaker and communicated via the patient's body to the surface EKG. Accordingly, marker code signals generated in reference to the pacemaker can 12 is not to be inferred as well.

While telemetry is the preferred method for sensing marker codes in the presence of a physician, the present invention is ideally adapted for extended patient monitoring wherein the marker codes can be sensed and recorded at home at any time with the patient. Thus, irregularities or concerns of the patient regarding the pacemaker performing which cannot be duplicated or ascertained in the presence of the physician can now be recorded at home with the patient and analyzed by the physician at a later time. Consequently, the physician will not have to speculate how the pacemaker was functioning when the patient was home and not in the presence of the physician when using a holter monitor.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

We claim:

1. A cardiac pacer apparatus, comprising:
   (a) a pacer housing including a conductive pacer can;
   (b) a first endocardial lead having a first electrode disposed thereon;
   (c) a second electrode disposed proximate said housing and insulated from the pacer can;
   (d) a pulse generator coupled to said endocardial lead for generating pace pulses; and
   (e) marker generator means coupled to said pacer can and said second electrode for generating marker codes therebetween as a function of said pulse generator activity.

2. The pacer apparatus as specified in claim 1 wherein said second electrode is disposed on said pacer housing and insulated from the pacer can.

3. The pacer apparatus as specified in claim 1 wherein said marker codes are generated at an electrical potential between 5 mV and 5 V.

4. The pacer apparatus as specified in claim 1 wherein said marker generator generates said marker codes nearly simultaneously when said pulse generator generates said pace pulses.

5. The pacer apparatus as specified in claim 1 wherein said first endocardial lead has a third electrode disposed thereon electrically isolated from said first electrode.

6. The pacer apparatus as specified in claim 1 further comprising a second endocardial lead having a third electrode disposed thereon.

7. A method of ascertaining cardiac pacer activity of a cardiac pacer apparatus coupled to a patient's heart using a two-channel holter monitor, said pacer apparatus having:
   (a) a pacer housing including a conductive pacer can;
   (b) a first endocardial lead having a first electrode disposed thereon;
   (c) a second electrode disposed proximate said housing and insulated from the pacer can;
   (d) a pulse generator coupled to said endocardial lead for generating pace pulses; and
   (e) marker generator means coupled to said pacer can and said second electrode for generating marker codes therebetween as a function of said pulse generator activity;
   The method comprising the steps of:
   (i) sensing and recording an EKG signal of the patient on the first channel of the holter monitor; and
   (ii) sensing said marker codes of the pacer apparatus generated proximate the pacer apparatus and recording on the second channel of the holter monitor.

8. The method as specified in claim 7 wherein said pacer apparatus generates said marker codes nearly simultaneously when said pace pulses are generated by said pulse generator.

* * * * *